US011562108B2

(12) United States Patent
Kim et al.

(10) Patent No.: US 11,562,108 B2
(45) Date of Patent: Jan. 24, 2023

(54) METHOD FOR ANALYZING SULFIDE-BASED SOLID ELECTROLYTE USING COMPUTER SIMULATION AND PROGRAM FOR ANALYZING SULFIDE-BASED SOLID ELECTROLYTE USING COMPUTER SIMULATION

(71) Applicant: KOREA INSTITUTE OF SCIENCE AND TECHNOLOGY, Seoul (KR)

(72) Inventors: Hyoung chul Kim, Seoul (KR); Byung Kook Kim, Seoul (KR); Hae Weon Lee, Seoul (KR); Jong Ho Lee, Seoul (KR); Ji Won Son, Seoul (KR); Hun Gi Jung, Seoul (KR); Ji Su Kim, Seoul (KR); Sung Jun Choi, Seoul (KR); Eu Deum Jung, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 1107 days.

(21) Appl. No.: 16/191,069

(22) Filed: Nov. 14, 2018

(65) Prior Publication Data

US 2019/0325096 A1 Oct. 24, 2019

(30) Foreign Application Priority Data

Apr. 23, 2018 (KR) .......................... 10-2018-0046630

(51) Int. Cl.
*G01N 33/48* (2006.01)
*G01N 33/50* (2006.01)
*G06F 30/20* (2020.01)
*H01M 10/0562* (2010.01)
*G16C 20/30* (2019.01)

(52) U.S. Cl.
CPC ............. *G06F 30/20* (2020.01); *G16C 20/30* (2019.02); *H01M 10/0562* (2013.01); *H01M 2300/0068* (2013.01)

(58) Field of Classification Search
CPC .............................. G16C 20/30; Y02E 60/10
See application file for complete search history.

(56) References Cited

FOREIGN PATENT DOCUMENTS

| JP | 2005-032058 A | 2/2005 | |
|---|---|---|---|
| JP | 4443797 B2 | 1/2010 | |
| JP | 2015-135790 A | 7/2015 | |
| KR | 10-1375672 B1 | 3/2014 | |
| KR | 10-1675348 B1 | 11/2016 | |
| KR | 10-2017-0084707 A | 7/2017 | |
| KR | 10-1772389 B1 | 8/2017 | |
| WO | WO-2018081808 A1 * | 5/2018 | ............. G16C 20/00 |

OTHER PUBLICATIONS

English machine translation of KR101375672. (Year: 2022).*
English machine translation of KR101675348. (Year: 2022).*
Communications of Korean Office Action dated Jul. 10, 2019 of Korean Patent Application No. 10-2018-0046630, which corresponds to this application.

* cited by examiner

*Primary Examiner* — Russell S Negin
(74) *Attorney, Agent, or Firm* — Goldilocks Zone IP Law

(57) ABSTRACT

Disclosed is a method for analyzing a sulfide-based solid electrolyte using computer simulation including connecting, by a user, to a client accessible to a server, inputting information of a sulfide-based solid electrolyte to be analyzed to the client, transmitting, by the client, the information to the server, implementing, by the server, generation of a three-dimensional structure in which anion clusters and lithium ions are disposed, based on the transmitted information, feeding back, by the server, an implementation result to the client, and displaying, by the client, the feedback result. In addition, properties of sulfide-based solid electrolytes, which cannot be observed by experimentation, can be analyzed based on lithium, ion conductivity.

15 Claims, 13 Drawing Sheets

Datasheet

Calculation-ID-000001

1. Energy hull: 0.04eV
   · Decomposition
   →$Li_2S + P_2S_5$

2. S sub-lattice:
   · HCP 65%, SC 20%, BCC 15%
   · Percolated S Sub-lattice→HCP 3. Bandgap: 2.54eV (insulator)
   · 1NN→3.02Å
   · 2NN→3.13eV 4. Estimated Li ion conducting level
   · gamma-$Li_3PS_4$
   · $Li_4P_2S_6$

METHOD FOR ANALYZING SULFIDE-BASED SOLID ELECTROLYTE USING COMPUTER SIMULATION AND PROGRAM FOR ANALYZING SULFIDE-BASED SOLID ELECTROLYTE USING COMPUTER SIMULATION

CROSS-REFERENCE TO RELATED APPLICATION

This application claims under 35 U.S.C. § 119(a), the benefit of priority to Korean Patent Application No 10-2018-0046630 filed on Apr. 23, 2018, the entire contents of which are incorporated herein by reference.

BACKGROUND

(a) Technical Field

The present invention relates to a method for analyzing a sulfide-based solid electrolyte using computer simulation and a program for analyzing a sulfide-based solid electrolyte using computer simulation. More specifically, the present invention relates to a method for analyzing a sulfide-based solid electrolyte using computer simulation and a program for analyzing a sulfide-based solid electrolyte using computer simulation that are capable of analyzing a sulfide-based solid electrolyte based on lithium ion conductivity.

(b) Background Art

Increasing interest in clean energy has recently brought about increasing demand to use a battery as an energy source for transport means. The battery includes a positive electrode, an electrolyte layer and a negative electrode. Recently, in order to improve stability of the electrolyte layer, the electrolyte layer is formed of a solid electrolyte. The generally used solid electrolyte is a sulfide-based solid electrolyte. As a result, research associated with methods for analyzing a sulfide-based solid electrolyte is increasing.

Experimentation showed that highly conductive sulfide-based solid electrolytes generally include a mixture of crystalline and glassy materials, and a lithium ion conduction route created by the crystalline material determines the overall conductivity of solid electrolytes. Due to the aforementioned feature and limited calculation efficiency regarding the glassy structure, most research on sulfide-based solid electrolytes using computer simulation has focused on research on lithium ion conductivity of crystalline materials. Sulfide-based crystalline high lithium ion-conductivity materials reported to date have the following two characteristics. The first characteristic is based on a thermodynamically meta-stable phase and the second characteristic is that an internal lattice structure including sulfur generally has a body-centered cubic structure. Most structure-forming programs find a stable structure based on thermodynamics, but do not evaluate a crystal structure based on lithium ion conductivity. Accordingly, although stable lithium ion-conducting solid electrolytes are found by electron- or atom-based simulation, they do not secure high lithium ion conductivity. In addition, due to limitation on efficiency of calculation costs and lack of interatomic potential, research on calculation of glassy structures and glass-ceramic combination structures must be the most challenging target.

Recently, research on increase in lithium ion conductivity of glassy structures due to changes in atomic structures has been reported. Glassy sulfides include thiophosphate ($P_xS_y$), which is a network former for lithium conduction, and a lithium ion, which is a network modifier. Amorphous sulfides include covalently bonded thiophosphate (network former) and ionically bonded lithium and sulfur (network modifier). Molecular anion clusters of glassy thiophosphate, which are experimentally identified, are $(PS_4)^{3-}$, $(P_2S_6)^{4-}$, and $(P_2S_7)^{4-}$. Although there was no accurate experimental report associated with a ratio of the anion clusters which are network formers, it was reported that lithium ion conductivity is changed depending on formation of respective anion clusters. When considering the fact that most sulfide-based materials, which have been solid electrolytes developed to date, are changed (modified) from glassy structures s a starting point to highly conductive glass-ceramic structures, research on formation of the molecular ions and thus changes in characteristics of glassy structures are very important.

Methods for forming glassy structures using electron or atom-based computer simulation are classified into two methods. The first method is to find a stable structure by inducing phase-transfer from a solid to a liquid at a high temperature and then cooling the same at a rapid rate. The second method is to form an arbitrary glassy structure and then stabilize the same. Each method has been used to from oxide-based glassy structures and amorphous organic molecular structures, but is distinguished from experimentally implemented sulfide electrolyte processes and is disadvantageously unsuitable for implementation of lithium-containing sulfide-based glassy structures into systematic configurations including a variety of molecular ions, and quantitative evaluation thereof.

Patent Document (Patent Document 1) Korean Patent No, 10-1375672
(Patent Document 2) Korean Patent No. 10-1772389

The above information disclosed in this Background section is provided only for enhancement understanding of the background of the invention and therefore it may contain information that does not form the prior art that is already known in this country to a person of ordinary skill n the art.

SUMMARY OF THE DISCLOSURE

The present invention has been made in an effort to solve the above-described problems associated with the prior art.

It is one object of the present invention to provide a method for simulating and analyzing a structure of a sulfide-based solid electrolyte using computer simulation, based on lithium ion conductivity.

It is another object of the present invention to provide a program for analyzing a sulfide-based solid electrolyte using computer simulation based on lithium ion conductivity.

In one aspect, the present invention provides method for analyzing a sulfide-based solid electrolyte using computer simulation including connecting, by a user, to a client accessible to a server, inputting information of a sulfide-based solid electrolyte to be analyzed to the client, transmitting, by the client, the information to the server, implementing, by the server, generation of a three-dimensional structure in which anion clusters and lithium ions are disposed, based on the transmitted information, feeding back, by the server, an implementation result to the client, and displaying, by the client, the feedback result.

The method for analyzing a sulfide-based solid electrolyte using computer simulation may include at least one of a method for simulating and analyzing a structure of a glassy-structure sulfide-based solid electrolyte, a method for simulating and analyzing a structure of a crystalline-structure sulfide-based solid electrolyte, and a method for generating and analyzing a glass-ceramic interface.

In the step of inputting, the information of the sulfide-based solid electrolyte may include at least one of a compositional ratio of $Li_2S$ and $P_2S_5$, a type of anion, clusters, which are a network former, a compositional ratio of anion clusters, a size of an area where anion clusters and lithium ions, which are a network modifier, are distributed, a shape of the area where anion clusters and lithium ions are distributed, a size of a unit cell constituting the area where anion clusters and lithium ions are distributed, a distribution state of lithium ions, and a distribution state of anion clusters.

When the method for analyzing a sulfide-based solid electrolyte using computer simulation is the method for simulating and analyzing a structure of a glassy-structure sulfide-based solid electrolyte, the step of implementing may include generating, by a simulation module of the server, the three-dimensional structure, calculating, by a computation module of the server, a physical property value of the three-dimensional structure, and screening, by an inspection module of the server, the sulfide-based solid electrolyte by comparing the physical property value with a predetermined reference physical property value in the server. In the step of feeding back, the server may feed back a result of each of the three-dimensional structure, the physical property value and the screening to the client. In the step of displaying the result, the client may display the result of each of the three-dimensional structure, the physical property value and the screening.

In the step of calculating the physical property value the computation module may calculate at least one, of an energy of a three-dimensional-structure, a mean, squared displacement, a radial distribution function, a density and a type of an internal lattice (sub-lattice) of sulfur.

When the method for analyzing a sulfide-based solid electrolyte using computer simulation is the method for simulating and analyzing a structure of a crystalline-structure sulfide-based solid electrolyte, the step of implementing may include generating the three-dimensional structure, calculating, by a first computation module of the server, a first physical property value of the three-dimensional structure of the sulfide-based solid electrolyte generated by the simulation module, based on molecular dynamics, firstly screening, by a first inspection module of the server, the sulfide-based solid electrolyte by comparing the first physical property value with a predetermined first reference physical property value in the server, defining, by a crystal structure definition module of the server, a crystal structure of the firstly screened sulfide-based solid electrolyte, calculating, by a second computation module of the server, a second physical property value of the sulfide-based solid electrolyte having the defined crystal structure, based on density functional theory, and secondly screening, by a second inspection module of the server, the sulfide-based solid electrolyte by comparing the second physical property value with a predetermined second reference physical property value in the server.

In the step of calculating the first physical property value, the first computation module may calculate at least one of a total energy of the three-dimensional structure of the sulfide-based solid electrolyte, and a type of an internal lattice of sulfur.

In the step of calculating the second physical property value, the second computation module may calculate at least one of a total energy of the sulfide-based solid electrolyte, an energy of an internal lattice of sulfur, mean squared displacement, electron structure, and migration energy barrier of lithium ions.

When the method for analyzing a sulfide-based solid electrolyte using computer simulation is the method for simulating and analyzing a structure of a crystalline-structure sulfide-based solid electrolyte, in the step of inputting, a block value corresponding to the three-dimensional structure may be input to the client, wherein the block value includes a network former, a network modifier, and a size of an area where the network former and the network modifier are disposed. The step of implementing may include generating the three-dimensional structure corresponding to the block value, evaluating a disposition type of the interior lattice of sulfur, implementing atom-based simulation, based on an evaluation result of the interior lattice of sulfur, defining a crystal structure of the sulfide-based solid electrolyte, based on a result of the atom-based simulation, and calculating a physical property value of the sulfide-based solid electrolyte by implementing electron-based simulation of the sulfide-based solid electrolyte having the defined crystal structure, based on density functional theory.

In the step of calculating the physical property value, the server ay calculate at least one of a total energy of the sulfide-based solid electrolyte, radial distribution function, mechanical property, electrical property, and an internal lattice of sulfur.

When the method for analyzing a sulfide-based solid electrolyte is the method for generating and analyzing a glass-ceramic interface, the step of the implementing may include generating a three-dimensional structure of a glassy-structure sulfide-based solid electrolyte, and a three-dimensional structure of a crystalline-structure sulfide-based solid electrolyte, generating a three-dimensional structure having an interface formed between the three-dimensional structure of the glassy-structure sulfide-based solid electrolyte and the three-dimensional structure of the crystalline-structure sulfide-based solid electrolyte bonded to each other in a certain direction, and generating a cross-sectional image of the three-dimensional structure taken in a certain direction. In the step of feeding back, the server may feed back the image to the client. In the step of displaying, the client may display the image.

In another aspect, the present invention provides a program for analyzing a sulfide-based solid electrolyte using computer simulation including a client for receiving information of a sulfide-based solid electrolyte and displaying an implementation result of a server, and a server for receiving the information from the client and feeding back the implementation result to the client. The server may include a simulation module for generating a three-dimensional structure of the sulfide-based solid electrolyte, and anion clusters and lithium ions may be disposed in the three-dimensional structure.

The program for analyzing a sulfide-based solid electrolyte using computer simulation may be a program for implementing at least one of simulating and analyzing a structure of a glassy-structure sulfide-based solid electrolyte, simulating and analyzing a structure of a crystalline-structure sulfide-based solid electrolyte, and generating and analyzing a glass-ceramic interface.

The program for analyzing a sulfide-based solid electrolyte using computer simulation may simulate and analyze a structure of a glassy-structure sulfide-based solid electrolyte, wherein the server further includes a computation module, and an inspection module. The computation module may receive data of the three-dimensional structure of the sulfide-based solid electrolyte from the simulation module and calculate a physical property value of the three-dimensional structure of the sulfide-based solid electrolyte, based on at least one theory of density functional theory and molecular dynamics. The inspection module may receive data of the physical property value from the computation module and screen the sulfide-based solid electrolyte by comparing the physical property value with a predetermined reference physical property value.

The program for analyzing a sulfide-based solid electrolyte using computer simulation may simulate and analyze a crystalline-structure sulfide-based solid electrolyte, wherein the server further includes crystal structure definition module for receiving firstly screened data and defining a crystal structure of the sulfide-based solid electrolyte, computation module, and an inspection module. The computation module may include a first computation module for receiving data of the three-dimensional structure of the sulfide-based solid electrolyte from the simulation module and calculating a first physical property value of the three-dimensional structure of the sulfide-based solid electrolyte based on molecular dynamics, and a second computation module for receiving data of the crystal structure from the crystal structure definition module and calculating a second physical property value of the sulfide-based solid electrolyte having the defined crystal structure, based on density functional theory. The inspection module may include a first inspection module for receiving data of the first physical property value from the first computation module and screening the sulfide-based solid electrolyte by comparing the first physical property value with a predetermined first reference physical property value, and a second inspection module for receiving data of the second physical property value from the second computation module and secondly screening the sulfide-based solid electrolyte by comparing the second physical property value with a predetermined second reference physical property value.

The program for analyzing a sulfide-based solid electrolyte using computer simulation may simulate and analyze a structure of a crystalline-structure sulfide-based solid electrolyte, wherein the client receives a block value corresponding to the three-dimensional structure, the block value includes a network former, a network modifier, and a size of an area where the network former and the network modifier are disposed. The server may include the simulation module for generating the three-dimensional structure corresponding to the block value, a first evaluation module for evaluating a disposition type of an interior lattice of sulfur present in the sulfide-based solid electrolyte, a first simulation module for receiving first evaluation data from the first evaluation module and implementing atom-based simulation, a crystal structure definition module for receiving first simulation data from the first simulation module and defining a crystal structure of the sulfide-based solid electrolyte, and a physical property value calculation module for receiving data of the crystal structure from the crystal structure definition module and calculating a physical property value of the sulfide-based solid electrolyte by implementing electron-based simulation of the electrolyte, based on density functional theory.

The program for analyzing a sulfide-based solid electrolyte using computer simulation may analyze generation of a glass-ceramic interface, wherein the simulation module includes a three-dimensional structure generation module for generating a three-dimensional structure of a glassy-structure sulfide-based solid electrolyte, and a three-dimensional structure of a crystalline structure sulfide-based solid electrolyte, a structure generation module for receiving data of the three-dimensional structure from the three-dimensional structure generation module and generating a three-dimensional structure having an interface formed between the three-dimensional structure of the glassy-structure sulfide-based solid electrolyte and the three-dimensional structure of the crystalline-structure sulfide-based solid electrolyte bonded to each other in a certain direction, and an image generation module for receiving data of the structure generation from the structure generation module and generating cross-sectional image of the three-dimensional structure taken in a certain direction. The client may receive data of the image from the image generation module and display the image.

Other aspects and preferred embodiments of the invention are discussed infra.

BRIEF DESCRIPTION OF THE DRAWINGS

The above and other features of the present invention will now be described in detail with reference to certain exemplary embodiments thereof illustrated in the accompanying drawings which are given hereinbelow by way of illustration only, and thus are not limitative of the present invention, and wherein.

DETAILED DESCRIPTION

Figure 1A:
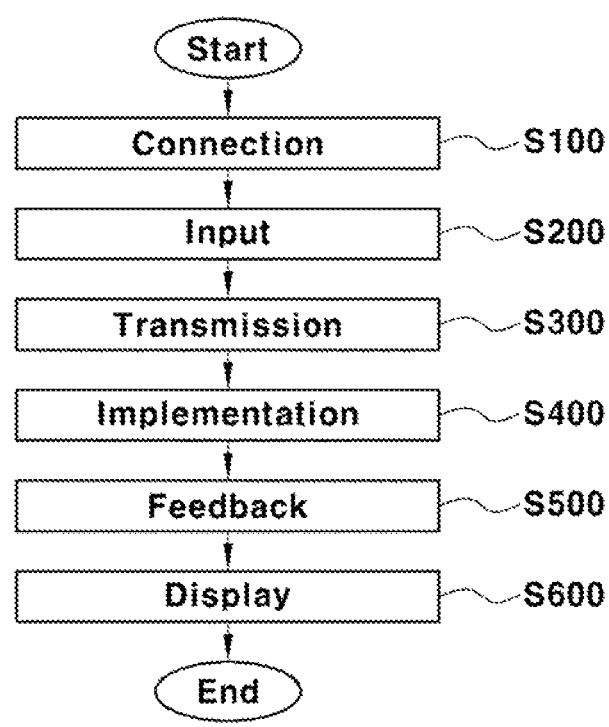
FIG. 1A is a schematic flowchart illustrating a method for analyzing a sulfide-based solid electrolyte using computer simulation according to an embodiment of the present invention.

The objects described above, and other objects, features and advantages will be clearly understood from the following preferred embodiments with reference to the annexed drawings. However, the present invention is not limited to the embodiments and may be embodied in different forms. The embodiments are suggested only to offer thorough and complete understanding of the disclosed context and sufficiently inform those skilled in the art of the technical concept of the present invention.

Like reference numbers refer to like elements throughout the description of the figures. In the drawings, the sizes of structures are exaggerated for clarity. It will be understood that, although the terms "first," "second", etc. may be used herein to describe various elements, these elements should not be limited by these terms and are used only to distinguish one element from another. For example, within the scope defined by the present invention, a first element may be referred to as a second element and, similarly, a second element may be referred to as a first element. Singular forms are intended to include plural forms as well, unless context clearly indicates otherwise.

It will be further understood that the terms "comprises" and/or "has", when used in this specification, specify the presence of stated features, numbers, steps, operations, elements, components or combinations thereof, but do not preclude the presence or addition of one or more other features, numbers, steps, operations, elements, components, or combinations thereof. In addition, it will be understood that, when an element such as a layer, film, region or substrate is referred to as being "on" another element, it can be directly on the other element or an intervening element may also be present. It will also be understood that when an element such as layer, film, region or substrate is referred to as being "under" another element, it can be directly under the other element or ah intervening element may also be present.

Hereinafter, a method for analyzing a sulfide-based solid electrolyte using computer simulation according to an embodiment of the present invention will be described in detail.

The term-"based" may include a compound corresponding to "~" or a derivative of "~". The term "derivative" means a compound which is modified from a certain compound as a precursor while retaining the structure and characteristics of the precursor such as introduction of a functional group, oxidation, reduction, or substitution of an atom.

Figure 1B:
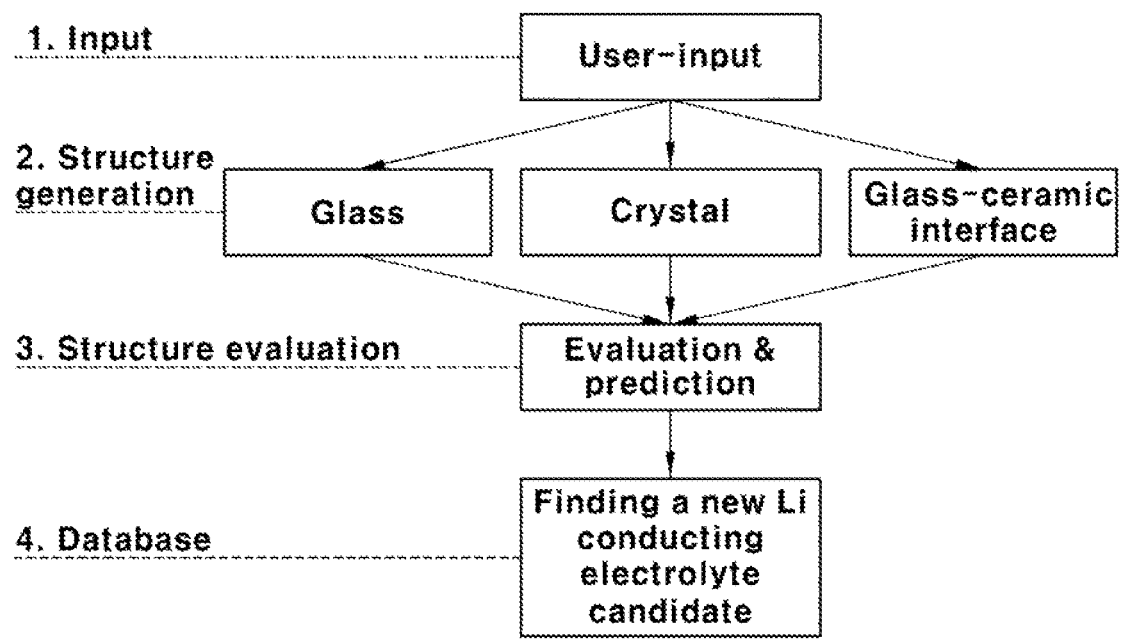
FIG. 1B is a schematic diagram illustrating a method, for analyzing a sulfide-based solid electrolyte using computer simulation according to the embodiment of the present invention.

FIG. 1A is a schematic flowchart illustrating a method for analyzing a sulfide-based solid electrolyte using computer simulation according to an embodiment of the present invention. FIG. 1B is a schematic diagram illustrating a method for analyzing a sulfide-based solid electrolyte using computer simulation according to the embodiment of the present invention.

Referring to FIGS. 1A and 1B, the method for analyzing a sulfide-based solid electrolyte using computer simulation according to an embodiment of the present invention includes connecting, by a user, to a client (100 of FIG. 7) accessible to a server (200 of FIG. 7) (S100), inputting information of a sulfide-based solid electrolyte to be analyzed to the client (100 of FIG. 7) (S200), transmitting, by the client (100 of FIG. 7), the information to the server (200 of FIG. 7) (S300), implementing, by the server (200 of FIG. 7), generation of a three-dimensional structure in which anion clusters and lithium ions are disposed, based on the transmitted information (S400), feeding back, by the server (200 of FIG. 7), an implementation result to the client (100 of FIG. 7) (S500) and displaying, by the client (100 of FIG. 7), the feedback result (S600).

The method for analyzing a sulfide-based solid electrolyte using computer simulation according to the embodiment of the present invention may be at least one of a method for simulating and analyzing a structure of a glassy-structure sulfide-based solid electrolyte, a method for simulating and analyzing a structure of a crystalline-structure sulfide-based solid electrolyte, and a method for generating and analyzing a glass-ceramic interface.

First, a user connects to a client (100 of FIG. 7) accessible to a server (200 of FIG. 7) (S100). There is no particular limitation as to the client (100 of FIG. 7) so long as it is accessible to the server (200 of FIG. 7) and can be connected by a user. For example, the client (100 of FIG. 7) may be an analysis program.

Information of a sulfide-based solid electrolyte to be analyzed is input to the client (100 of FIG. 7) (S200). In the step of inputting (S200), the information of the sulfide-based solid electrolyte may include at least one of a compositional ratio of $Li_2S$ and $P_2S_5$, a type of anion clusters, a compositional ratio of anion clusters, a size of an area where anion clusters and lithium ions are distributed, a shape of the area where anion clusters and lithium ions are distributed, a size of a unit cell constituting the area where anion clusters and lithium ions are distributed, a distribution state of lithium ions, and a distribution state of anion clusters.

For example, the cross-sectional shape of the area where anion clusters and lithium ions are distributed may have a variety of shapes such as a rectangle, a diamond and a trapezoid. Regarding the distribution states of lithium ions and anion clusters, the lithium ions and anion clusters may be randomly distributed and distributed manually upon receiving a certain value.

Figures 6, 7:
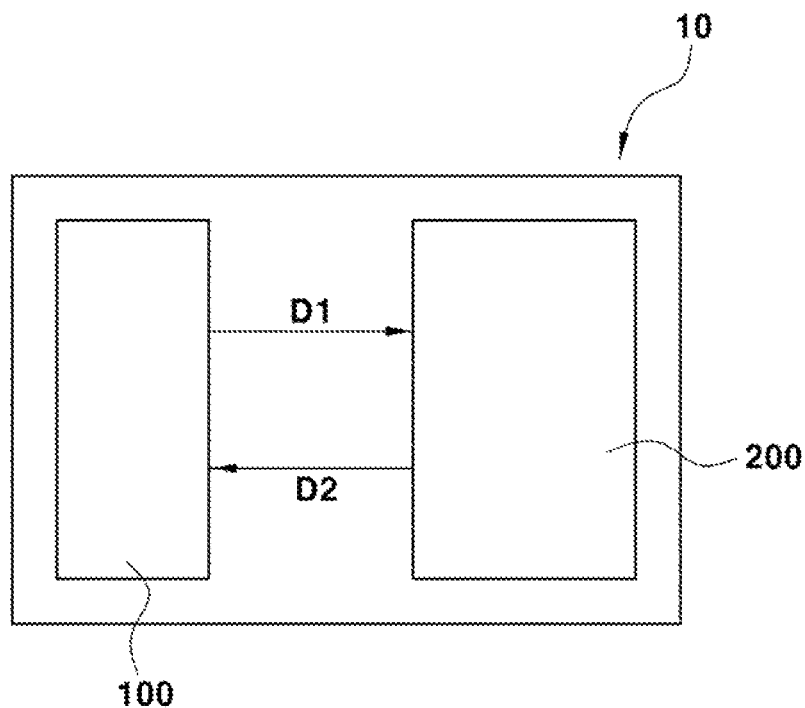
FIG. 6 exemplarily illustrates an analysis result displayed by the client.
FIG. 7 is a schematic block diagram illustrating a program for analyzing a sulfide-based solid electrolyte using computer simulation according to an embodiment of the present invention.

For example, in the step of inputting (S200), an initial parameter, cell information and molecular selection may be input to the client (100 of FIG. 7). The initial parameter ay include at least one of a compositional ratio of $Li_2S$ and $P_2S_5$, a type of anion clusters, which are a network former, and a compositional ratio of the anion clusters. The cell information may include at least one of size of the area where anion clusters and lithium ions, which are a network modifier, are distributed, a shape of the area where anion clusters and lithium ions are distributed, and a size of a unit cell constituting the area where anion clusters and lithium ions are distributed. The molecular selection may include at least one of a distribution state of lithium ions and a distribution state of anion clusters.

The client (100 of FIG. 7) transmits information to the server (200 of FIG. 7) (S300). The client (100 of FIG. 7) transmits the information supplied in the step of inputting (S200) to the server (200 of FIG. 7).

The server (200 of FIG. 7) implements gene n of a three-dimensional structure in which anion clusters and lithium ions are distributed, based on the transmitted information (S400). Regarding the method for analyzing a sulfide-based solid electrolyte using computer simulation according to the embodiment of the present invention, the size of the area where anion clusters and lithium ions are distributed, and the size of a unit cell constituting the area where anion clusters and lithium ions a distributed can be adjusted to small levels of 0.3 nm to 10 nm, so that the distances between anion clusters and lithium ions can be reduced. When the distance between anion clusters is set to a small level, a dense glass structure with a stronger binding force and smaller free volume can be found and there an effect of identifying formation possibility of a new anion including a plurality of basic anion clusters linked to one another. When the distance between anion clusters is set to a great level, a low-energy structure can be found because of increased degree of freedom regarding arrangement shapes of anions and cations.

The server (200 of FIG. 7) feeds back an implementation result to the client (100 of FIG. 7) (S500). For example when, in the step of implementing (S400), a three-dimensional structure of the sulfide-based solid electrolyte is generated, in the step of feeding back (S500), the server (200 of FIG. 7) can feed back a result of the three-dimensional structure to the client (100 of FIG. 7).

The client (100 of FIG. 7) displays the feedback result (S600). For example, when, in the step of feeding back (S500), the result of the three-dimensional structure of the sulfide-based solid electrolyte is fed back to the client (100 of FIG. 7), in the step of displaying the result (S600), the client (100 of FIG. 7) can display the result of the three-dimensional structure.

Figure 2A:
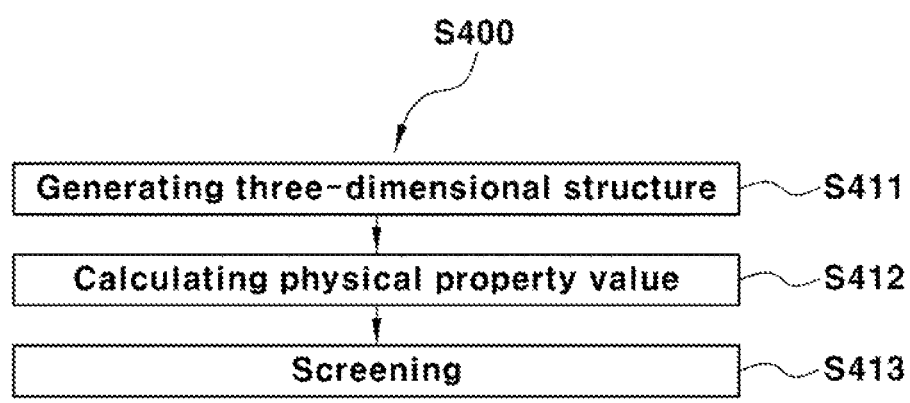
FIG. 2A is a schematic flowchart illustrating a step of implementation, when the method for analyzing a sulfide-based solid electrolyte using computer simulation according to the embodiment of the present invention is a method for simulating and analyzing a structure of a glassy-structure sulfide-based solid electrolyte.
Figure 2B:
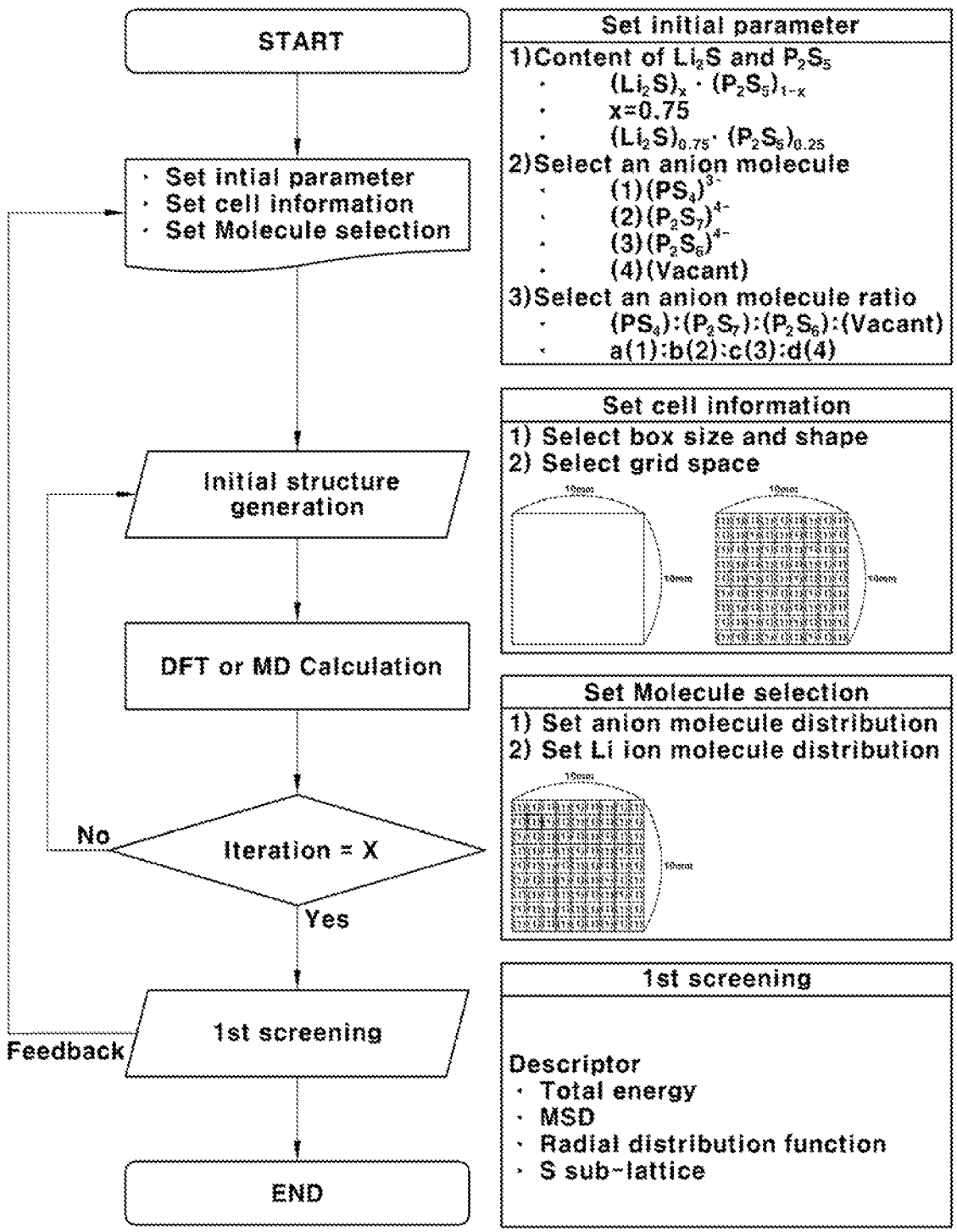
FIG. 2B is an algorithm flowchart, when the method for analyzing a sulfide-based solid electrolyte using computer simulation according to the embodiment of the present invention is a method for simulating and analyzing a structure of a glassy-structure sulfide-based solid electrolyte.

FIG. 2A is a schematic flowchart illustrating a step of implementation, when the method for analyzing a sulfide-based solid electrolyte using computer simulation according to the embodiment of the present invention is a method for simulating and analyzing a structure of a glassy-structure sulfide-based solid electrolyte. FIG. 2B is an algorithm flowchart, when the method for analyzing a sulfide-based solid electrolyte using computer simulation according to the embodiment of the present invention is a method for simulating and analyzing a structure of a glassy-structure sulfide-based solid electrolyte.

Referring to FIGS. 2A and 2B, when the method for analyzing a sulfide-based solid electrolyte using computer simulation according to the embodiment of the present invention is a method for simulating and analyzing a structure of a glassy-structure sulfide-based solid electrolyte, the step of implementing (S400) may include generating a three-dimensional structure (S411), calculating a physical property value (S412) and screening (S413).

In the step of generating a three-dimensional structure (S411), a simulation module of the server (200 of FIG. 7) generates a three-dimensional structure of the sulfide-based solid electrolyte. Information is received in the step of inputting (S200), and a three-dimensional structure is generated based on set composition, lattice structure and distribution of thiophosphate molecules and lithium ions in the step of generating a three-dimensional structure (S411). This can be carried out by atom- or electron-based computer simulation.

The step of generating a three-dimensional structure of the sulfide-based solid electrolyte (S411) may include generating an area, depending on the size of the area where anion clusters and lithium ions are distributed, the shape of the area where anion clusters and lithium ions are distributed, and the size of a unit cell constituting the area where anion clusters and lithium ions are distributed, and then distributing the anion dusters and the lithium ions in the area.

In the step of calculating a physical property value (S412), a computation module of the server (200 of FIG. 7) calculates a physical property value of the three-dimensional structure of the sulfide-based solid electrolyte, based on at least one theory of density functional theory and molecular dynamics. In the step of calculating a physical property value (S412), the physical property value may be calculated by atom- or electron-based computer simulation. In the step of calculating a physical property value (S412), the computation module may calculate at least one of an energy of the three-dimensional structure, n can squared displacement, radial distribution function, density, and type of an internal lattice (sub-lattice) of sulfur.

In the step of screening (S413), an inspection module of the server (200 of FIG. 7) screens the sulfide-based solid electrolyte by comparing the calculated physical property value with a predetermined reference physical property value in the server (200 of FIG. 7). More specifically, the inspection module can screen an electrolyte candidate capable of highly conducting lithium ions by converting the physical property value into a database. The predetermined reference physical property value may be, for example, at least one of a total energy of various sulfide-based solid electrolytes, an energy of an internal lattice of sulfur, a type of an internal lattice of sulfur, mean squared displacement, an electron structure, and a migration energy barrier of lithium, ions, which, is previously stored in the server (200 of FIG. 7). Through screening, the electrical, mechanical and chemical properties of the sulfide-based solid electrolyte can be determined and n electrolyte to which the sulfide-based solid electrolyte has similar properties can be determined.

In the step of feeding back (S500), the server (200 of FIG. 7) feeds back a result of each of the three-dimensional structure of the sulfide-based solid electrolyte, the physical property value and the screening to the client (100 of FIG. 7).

In the step of displaying the result (S600), the client (100 of FIG. 7) displays each feedback result of the three-dimensional structure of the sulfide-based solid electrolyte, the physical property value and the screening.

Figure 3A:
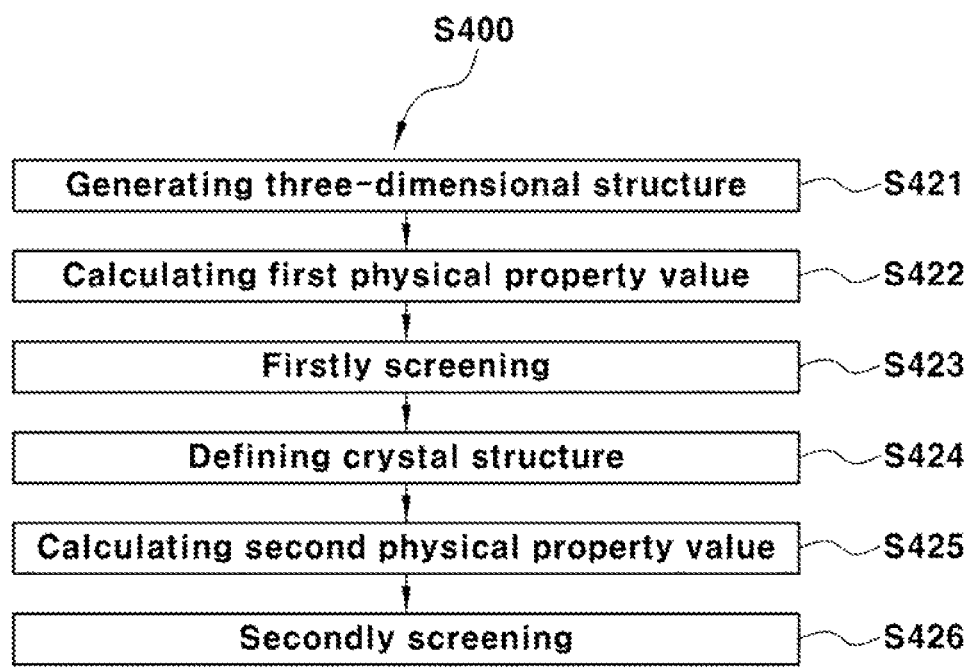
FIG. 3A is a schematic flowchart illustrating a step of implementation, when the method for analyzing a sulfide-based solid electrolyte using computer simulation according to the embodiment of the present invention is a method for simulating and analyzing a structure of a crystalline-structure sulfide-based solid electrolyte.
Figure 3B:
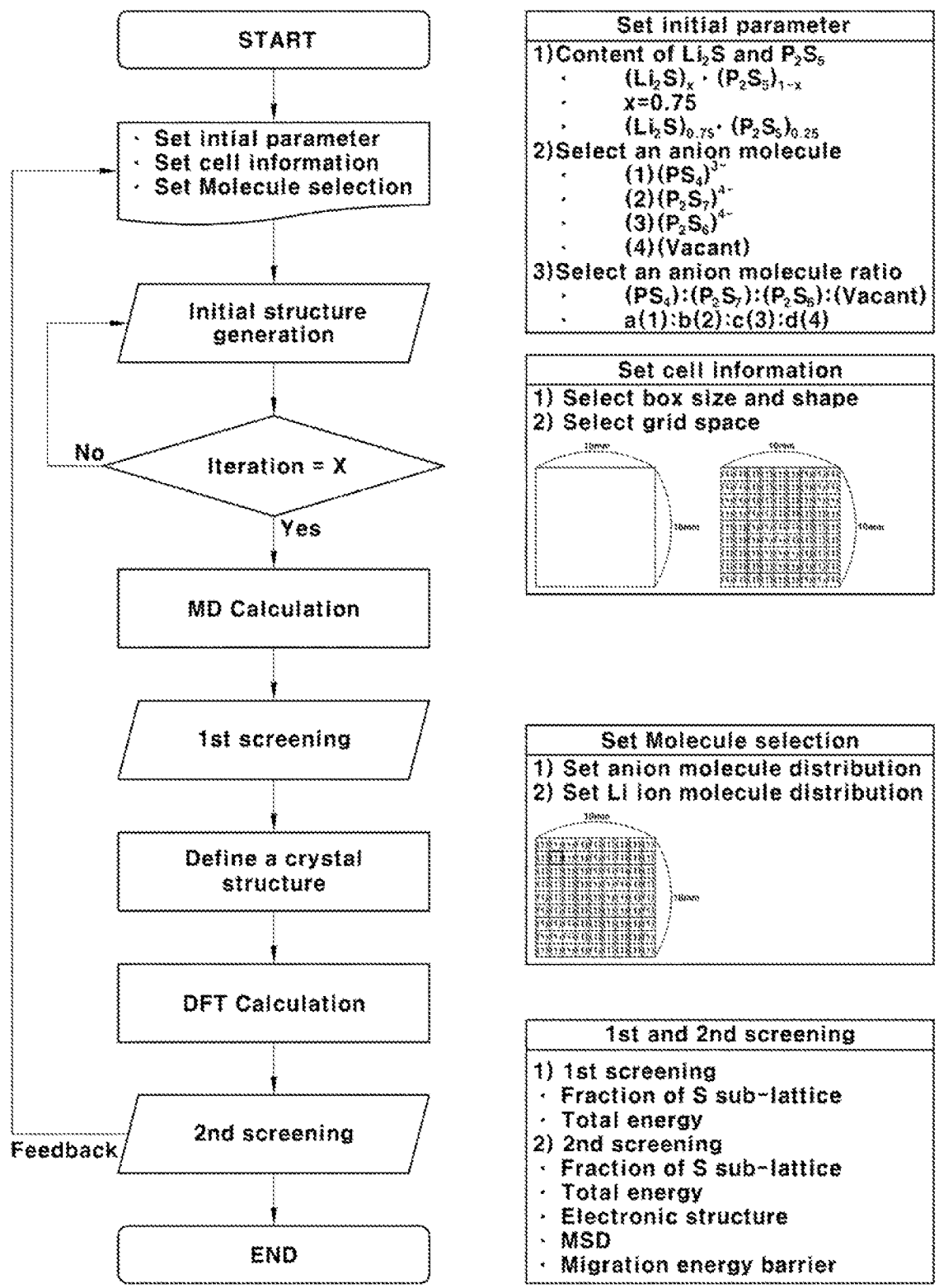
FIG. 3B is an algorithm flowchart, when the method for analyzing a sulfide-based solid electrolyte using computer simulation according to the embodiment of the present invention is a method for simulating and analyzing a structure of a crystalline-structure sulfide-based solid electrolyte.

FIG. 3A is a schematic flowchart illustrating a step of implementation, when the method for analyzing a sulfide-based solid electrolyte using computer simulation according to the embodiment of the present invention is a method for simulating and analyzing a structure of a crystalline-structure sulfide-based solid electrolyte. FIG. 3B is an algorithm flowchart, when the method for analyzing a sulfide-based solid electrolyte using computer simulation according to the embodiment of the present invention is a method for simulating and analyzing a structure of a crystalline-structure sulfide-based solid electrolyte.

FIGS. 3A and 3B illustrate a method for simulating and analyzing a structure of a crystalline-structure sulfide-based solid electrolyte not enabling a user to directly recognize how anion clusters and lithium ions are distributed in an area.

Referring to FIGS. 3A and 3B, the method for analyzing a sulfide-based solid electrolyte using computer simulation according to the embodiment of the present invention may be a method for simulating and analyzing a structure of a crystalline-structure sulfide-based solid electrolyte. In this case, the step of implementing (S400) may include generating, by a simulation module of the server (200 of FIG. 7), a three-dimensional structure of the sulfide-based solid electrolyte (S421), calculating, by a first computation module of the server (200 of FIG. 7), a first physical property value of the three-dimensional structure of sulfide-based solid electrolyte generated by the simulation module, based on molecular dynamics (S422), firstly screening, by a first inspection module of the server (200 of FIG. 7), the sulfide-based solid electrolyte by comparing the first physical property value with a predetermined first reference physical property value in the server (200 of FIG. 7) (S423), defining, by a crystal structure definition module of the server (200 of FIG. 7), a crystal structure of the firstly screened sulfide-based solid electrolyte (S424), calculating, by a second computation module of the server (200 of FIG. 7), a second physical property value of the sulfide-based solid electrolyte having the defined crystal structure, based on density functional theory (S425), and secondly screening, by a second inspection module of the server (200 of FIG. 7), the sulfide-based solid electrolyte by comparing the second physical property value with a predetermined second reference physical property e in the server (200 of FIG. 7) (S426).

In the step of calculating the first physical property value (S422), the first computation module tray calculate at least one of a total energy of the sulfide-based solid electrolyte and a type of an internal lattice of sulfur. The predetermined first reference physical property value may be, for example, at least one of a total energy of various sulfide-based solid electrolytes and a type of an internal lattice of sulfur, which is previously stored in the server (200 of FIG. 7).

In the step of defining a crystal structure of the sulfide-based solid electrolyte (S424), the crystal structure of the sulfide-based solid electrolyte may be defined by evaluating grain symmetry of the sulfide-based solid electrolyte. The crystal structure of the sulfide-based solid electrolyte may mean a crystal structure such as an argyrodite or cubic structure.

In the step of calculating a second physical property value (S425), the second computation module may calculate at least one of a total energy of the sulfide-based solid electrolyte, an energy of an lattice of sulfur, mean squared displacement, electron structure, and migration energy barrier of lithium ions. The predetermined second reference physical property value may be, for example, at least one of a total energy of various sulfide-based solid electrolytes, an energy of an internal lattice of sulfur, mean squared displacement, electron structure, and migration energy barrier of lithium ions, which is previously stored in the server (200 of FIG. 7).

Figure 4A:
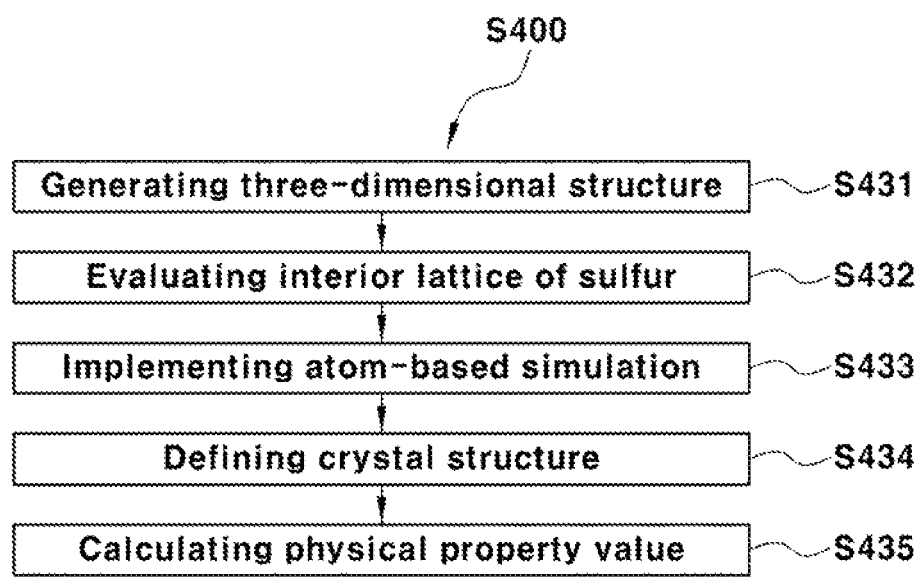
FIG. 4A is a schematic flowchart illustrating a step of implementation, when the method for analyzing a sulfide-based solid electrolyte using computer simulation according to an embodiment of the present invention is a method for simulating and analyzing a structure of a crystalline-structure sulfide-based solid electrolyte.
Figure 4B:
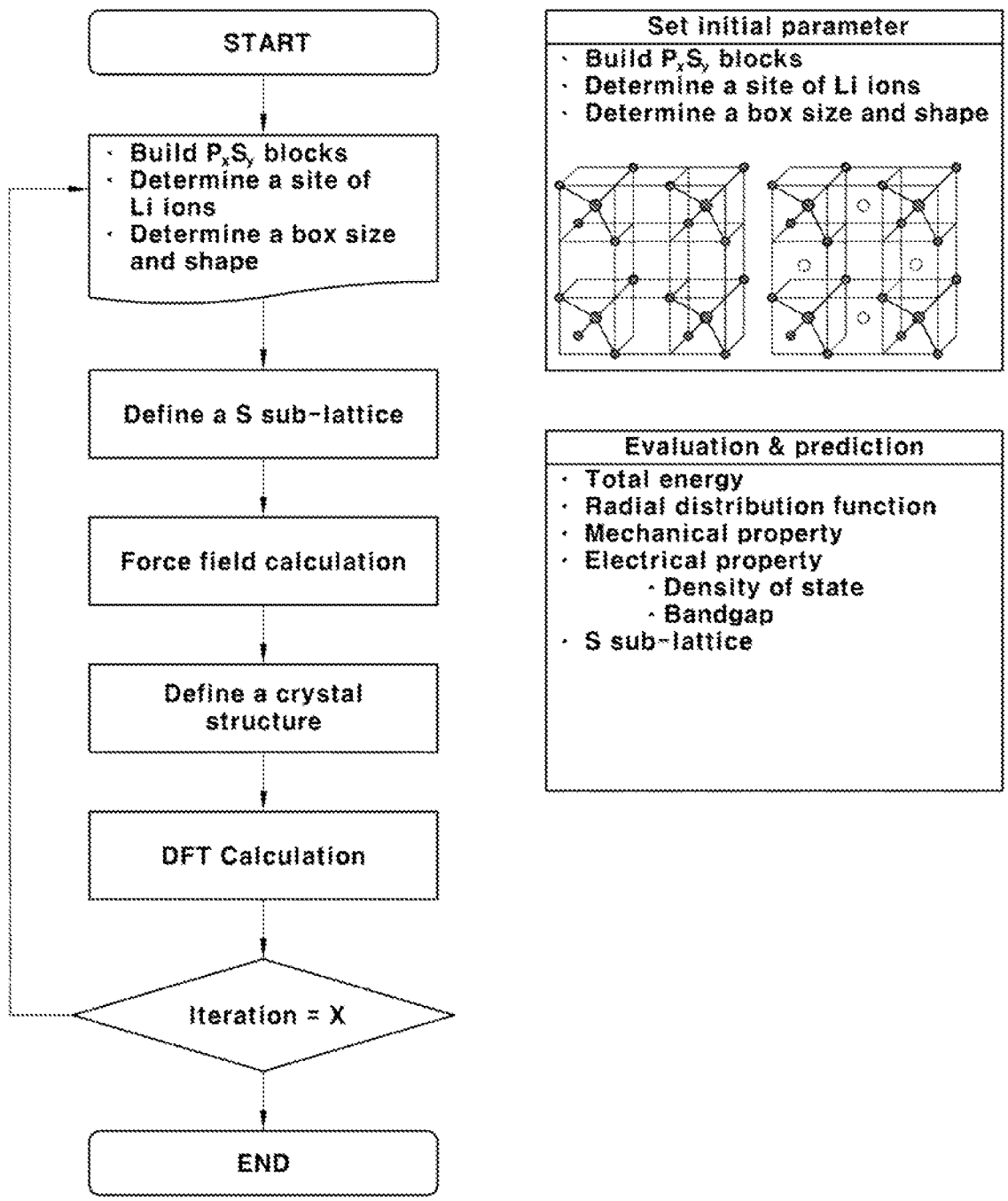
FIG. 4B is an algorithm flowchart, when the method for analyzing a sulfide-based solid electrolyte using computer simulation according to the embodiment of the present invention is a method for simulating and analyzing a structure of a crystalline-structure sulfide-based solid electrolyte.

FIG. 4A is a schematic flowchart illustrating a step of implementation, when the method for analyzing a sulfide-based solid electrolyte using computer simulation according to an embodiment of the present invention is a method for simulating and analyzing a structure of a crystalline-structure sulfide-based solid electrolyte. FIG. 4B is an algorithm flowchart, when the method for analyzing a sulfide-based solid electrolyte using computer simulation according to the embodiment of the present invention is a method for simulating and analyzing a structure of a crystalline-structure sulfide-based solid electrolyte.

FIGS. 4A and 4B illustrate a method for simulating and analyzing a structure of a crystalline-structure sulfide-based solid electrolyte that a user can directly recognize how anion clusters serving as a network former and lithium ions serving as a network modifier are distributed in an area. The client directly receives a block value, so that direct recognition (immediacy) of the user can be improved. This will be described later in more detail.

Referring to FIGS. 4A and 4B, the method for analyzing a sulfide-based solid electrolyte using computer simulation according to the embodiment of the present invention may be a method for simulating and analyzing a structure of a crystalline-structure sulfide-based solid electrolyte. In this case, in the step of inputting (S200), a block value corresponding to a three-dimensional structure is input to the client (100 of FIG. 7). The block value includes a network former, a network modifier, and a size of an area where the network former and the network modifier are disposed. The network former may mean thiophosphate, for example, $P_xS_y$. X and y may be each a natural number. For example, $P_xS_y$ may be at least one of $PS_4$, $P_2S_6$, and $P_2S_7$. The network modifier may be, for example, a lithium ion.

The step of implementing (S400) may include generating the three-dimensional structure corresponding to the block value (S431), evaluating a disposition type of an interior lattice of sulfur (S432), implementing atom-based simulation, based on the evaluation result of the interior lattice of sulfur (S433), defining a crystal structure of the sulfide-based solid electrolyte, based on the result of the atom-based simulation (S434), and calculating a physical property value of the sulfide-based solid electrolyte by implementing electron-based simulation of the sulfide-based solid electrolyte having the defined crystal structure, based on density functional theory (S435).

In the evaluating the disposition type of the interior lattice of sulfur (S432), whether the type of the internal lattice of sulfur is a body-centered cubic (BCC), hexagonal close-packed (HCP) or face-centered cubic (FCC) lattice can be identified. Whether or not the internal lattice of sulfur has a BCC structure can be identified, since the BCC structure has high ion conductivity. In the step of calculating a physical property value (S435), the server (200 of FIG. 7) may calculate at least one of a total energy of the sulfide-based solid electrolyte, radial distribution function, mechanical property, electric property and internal lattice of sulfur.

Figure 5A:
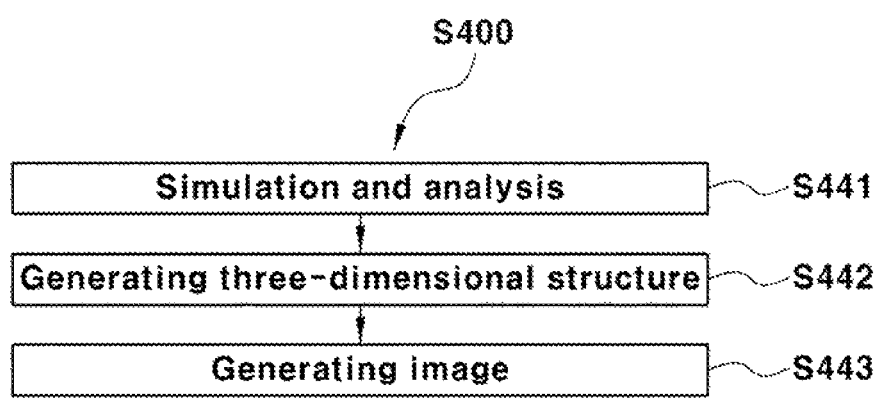
FIG. 5A is a schematic flowchart illustrating a step of implementation, when the method for analyzing a sulfide-based solid electrolyte using computer simulation according to the embodiment of the present invention is a method for generating and analyzing a glass-ceramic interface.
Figure 5B:
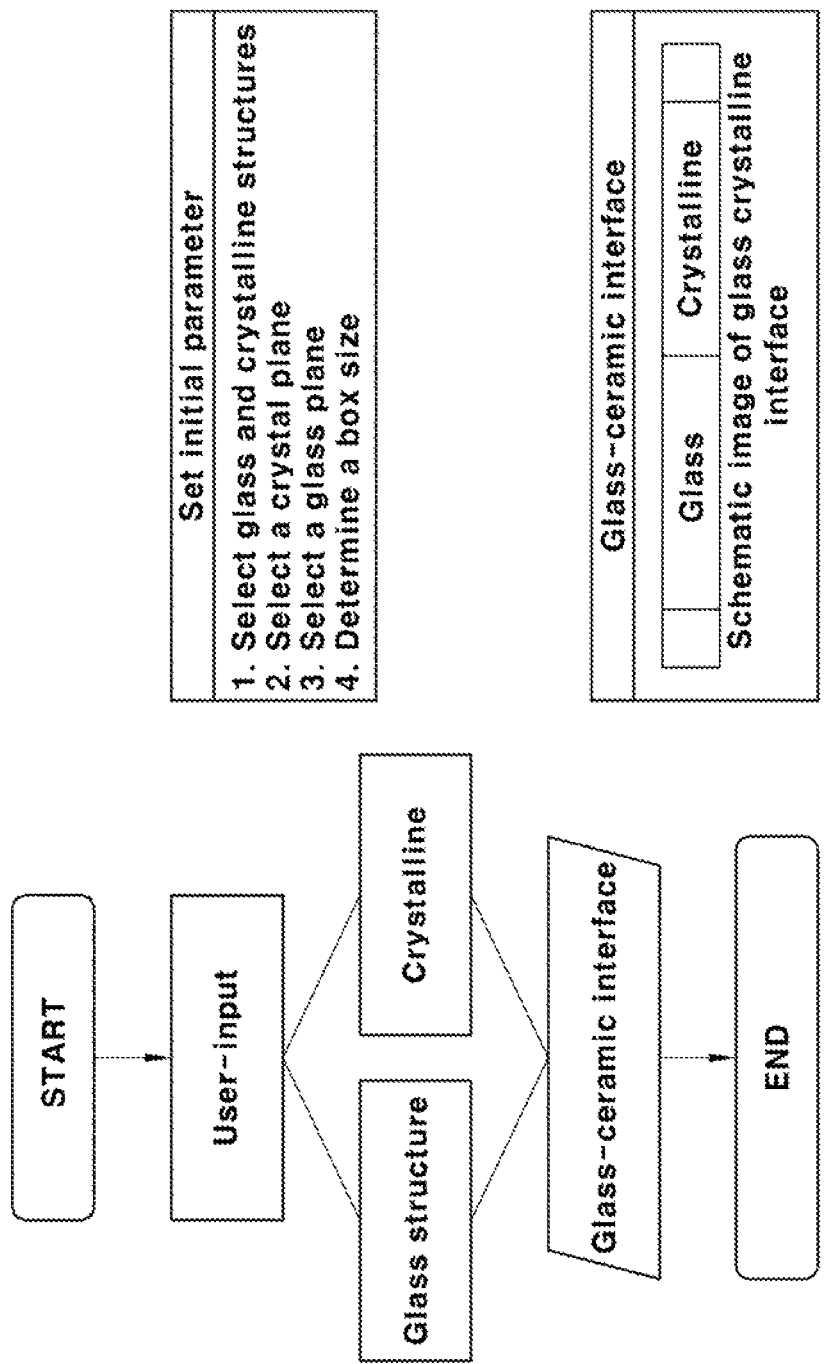
FIG. 5B is an algorithm flowchart, when the method for analyzing, a sulfide-based solid electrolyte using computer simulation according to the embodiment of the present invention is a method for generating and analyzing a glass-ceramic interface.

FIG. 5A is a schematic flowchart illustrating a step of implementation, when the method for analyzing a sulfide-based solid electrolyte using computer simulation according to the embodiment of the present invention is a method for generating and analyzing a glass-ceramic interface. FIG. 5B is an algorithm flowchart, when the method for analyzing a sulfide-based solid electrolyte using computer simulation according to the embodiment of the present invention is a method for generating and analyzing a glass-ceramic interface.

Referring to FIGS. 5A and 5B, the method for analyzing a sulfide-based solid electrolyte using computer simulation according to the embodiment of the present invention may be a method for generating and analyzing a glass-ceramic interface. In this case, the step of implementing (S400) may include generating a three-dimensional structure of a glassy-structure sulfide-based solid electrolyte, and a three-dimensional structure of a crystalline-structure sulfide-based did electrolyte (S441), generating a three-dimensional structure having an interface formed between the three-dimensional structure of the glassy-structure sulfide-based solid electrolyte and the three-dimensional structure of the crystalline-structure sulfide-based solid electrolyte bonded to each other in a certain direction (S442), and generating a cross-sectional image of the three-dimensional structure taken in a certain direction (S443).

In the step of generating a three-dimensional structure of a glassy-structure sulfide-based solid electrolyte, and a three-dimensional structure of a crystalline-structure sulfide-based solid electrolyte (S441), the three-dimensional structure of the glassy-structure sulfide-based solid electrolyte may be a structure in which anion clusters and lithium ions are each distributed in an area. The three-dimensional structure of the crystalline-structure sulfide-based solid electrolyte may be a structure in which anion clusters and lithium ions are each distributed in an area.

In the step of generating a three-dimensional structure having an interface (S442), the three-dimensional structure having an interface may be, for example, a three-dimensional structure that is the most stable, when the three-dimensional structure of the glassy-structure sulfide-based solid electrolyte and the three-dimensional structure of the crystalline-structure sulfide-based solid electrolyte are bonded to each other in a certain direction.

In the step of generating a cross-sectional image of the three-dimensional structure taken in a certain direction (S443), for example, a cross-sectional image of the three-dimensional structure taken in a certain direction such as XY, YZ or XZ may be generated.

In the step of feeding back (S500), the server (200 of FIG. 7) feeds back the image to the client (100 of FIG. 7). In the step of display (S600), the client (100 of FIG. 7) may display the image.

FIG. 6 exemplarily illustrates the analysis result displayed by the client. Referring to FIG. 6, the client (100 of FIG. 7) receives an implementation result from the server (200 of FIG. 7) and displays the implementation result.

Conventional analysis methods for generating structures are analysis methods generally used for electron- and atom-based computer simulation. Most analysis methods include only a structure for analyzing a certain property regarding calculation of material properties supporting internally. When the generation and analysis of the three-dimensional structure of the sulfide-based solid electrolytes are carried out by electron or atom-based computer simulation, great amounts of calculation results are generated. In addition, arrangement of enumerated results also requires lots of time and effort. Accordingly, there is a limitation of not supporting structural properties of sulfide-based solid electrolytes based inn anion clusters.

With the method for analyzing a sulfide-based solid electrolyte using computer simulation according to the embodiment of the present invention, experimental phenomena can be easily and rapidly analyzed by electron- or atom based computer simulation and thus new solid electrolyte materials can be designed. In addition properties of sulfide-based solid electrolytes, which cannot be observed by experimentation, can be analyzed based on lithium ion conductivity. Furthermore, properties of sulfide-based solid electrolytes can be analyzed without generating real prototypes.

Hereinafter, a program for analyzing a sulfide based solid electrolyte using computer simulation according to an embodiment of the present invention will be described. The following description will focus on details of different features from the aforementioned method for analyzing a sulfide-based solid electrolyte using computer simulation according to the embodiment and omitted features will follow the aforementioned method for analyzing a sulfide-based solid electrolyte using computer simulation.

FIG. 7 is a schematic block diagram illustrating a program for analyzing a sulfide-based solid electrolyte using computer simulation according to an embodiment of the present invention.

Referring to FIG. 7, the program 10 for analyzing a sulfide-based solid electrolyte using computer simulation according, to the embodiment includes a client 100 and a server 200. The program for analyzing a sulfide-based solid electrolyte using computer simulation according to the embodiment may be a program that implements t least one of: simulating and analyzing a structure of a glassy-structure sulfide-based solid electrolyte; simulating and analyzing a structure of a crystalline-structure sulfide-based solid electrolyte; and generating and analyzing a glass-ceramic interface.

The client 100 receives information of a sulfide-based solid electrolyte and displays an implementation result of the server 200. The server 200 receives information D1 from the client 100 and feeds back an implementation result D2 to the client 100.

Figure 8A:
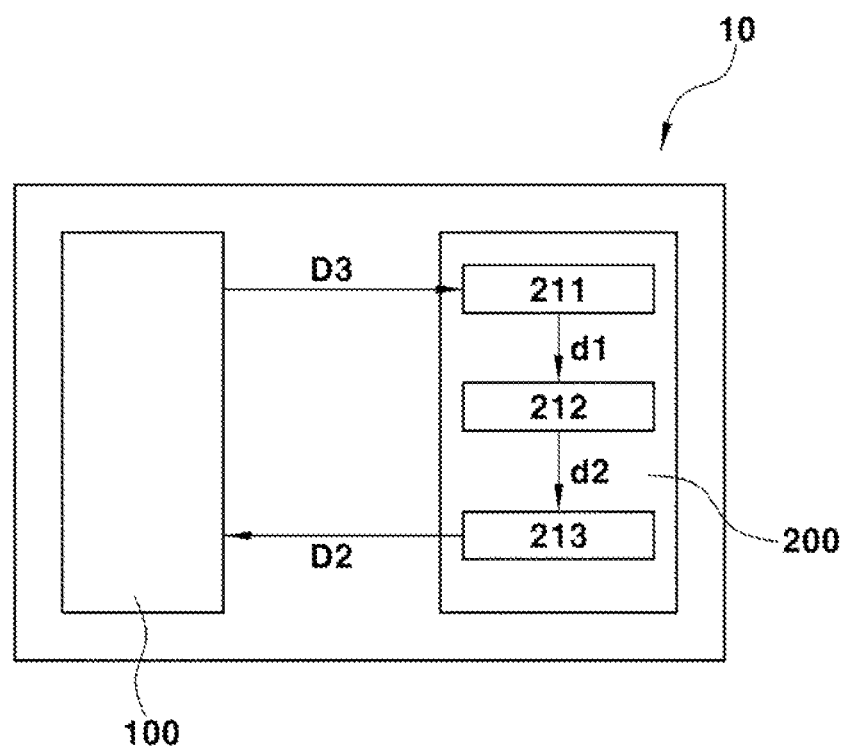
FIG. 8A is a schematic block diagram of an analysis program, when the program for analyzing a sulfide-based solid electrolyte using computer simulation according to the embodiment simulates and analyzes a glassy structure sulfide-based solid electrolyte.

The server 200 includes a simulation module (211 of FIG. 8A). The simulation nodule (211 of FIG. 8A) generates a three-dimensional structure of the sulfide-based solid electrolyte. Anion clusters and lithium ions are disposed in the three-dimensional structure.

FIG. 8A is a schematic block diagram of an analysis program, when the program for analyzing a sulfide-based solid electrolyte using computer simulation according to the embodiment simulates and analyzes a glassy structure sulfide-based solid electrolyte.

Referring to FIGS. 7 and 8A, the program 10 for analyzing a sulfide-based solid electrolyte using computer simulation according to the embodiment may simulate and analyze the structure of the glassy-structure sulfide-based solid electrolyte.

Upon receiving information, the client 100 transmits input information D3 to the server 200. The server 200 further includes a computation module 212 and an inspection module 213.

Upon receiving three-dimensional structure data d1 of the sulfide-based solid electrolyte from a simulation module 211, the computation module 212 calculates a physical property value of the three-dimensional structure of the sulfide-based solid electrolyte, based on at least one theory of density functional theory and molecular dynamics. Upon receiving physical property value data d2 from the computation module 212, the inspection module 213 screens the sulfide-based solid electrolyte by comparing the physical property value with a predetermined reference physical property value.

The server 200 may feedback data D4 of the computation module 212 of the client 100. The data D4 of the computation module 212 may include at least one of the three-dimensional structure, the physical property value and the screening result. The client 100 displays the data D4 of the computation module 212.

Figure 8B:
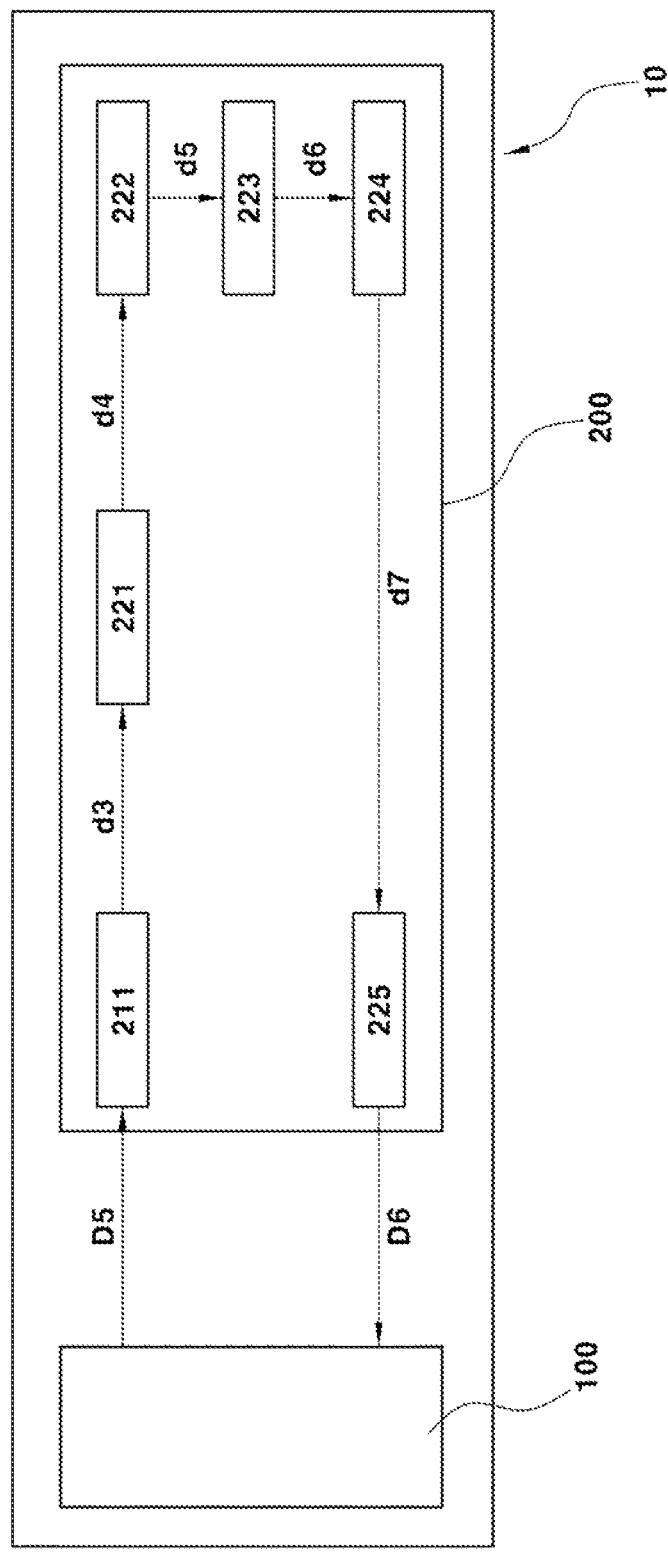
FIG. 8B is a schematic block diagram of an analysis program, when the program for analyzing a sulfide-based solid electrolyte using computer simulation according to the embodiment simulates and analyzes a crystalline-structure sulfide based solid electrolyte.

FIG. 8B is a schematic block diagram of an analysis program, when the program for analyzing a sulfide-based solid electrolyte using computer simulation according to the embodiment simulates and analyzes a structure of a crystalline-structure sulfide-based solid electrolyte.

Referring to FIGS. 7 and 8B, the program 10 for analyzing sulfide-based solid electrolyte using computer simulation according to the embodiment may simulate and analyze the crystalline-structure sulfide-based solid electrolyte.

FIG. 8B illustrates a program for simulating and analyzing a structure of a crystalline-structure sulfide-based solid electrolyte not enabling a user to directly recognize bow anion clusters and lithium ions are distributed in an area.

Upon receiving information, the client 100 transmits input information D5 to the server 200. The server 200 further includes a crystal structure definition module 223. The server 200 further includes a computation module 212 and an inspection module 213. The computation module 212 further includes a first computation module 221 and a second computation module 224. The inspection module 213 further includes a first inspection module 222 and a second inspection module 225.

Upon receiving three-dimensional structure data d3 of the sulfide-based solid electrolyte from a simulation module 211, the first computation module 221 calculates a first physical property value of the three-dimensional structure of the sulfide-based solid electrolyte, based on molecular dynamics. Upon receiving first physical property value data d4 from the first computation module 221, the first inspection module 222 firstly screens the sulfide-based solid electrolyte by comparing the first physical property value with a predetermined first reference physical property value. Upon receiving firstly screened data d5, the crystal structure definition module 223 defines a crystal structure of the sulfide-based solid electrolyte. Upon receiving crystal structure data d6 from the crystal structure definition module 223, the second computation module 224 calculates second physical property value of the sulfide-based solid electrolyte having the defined crystal structure, based on density functional theory. Upon receiving second physical property value data d7 from the second computation module 224, the second inspection module 225 secondly screens the sulfide-based solid electrolyte by comparing the second physical property value with a predetermined second reference physical property value.

The server 200 may feedback of data d6 of the computation module 212 of the client 100. The data d6 of the computation module 212 may include at least one of the three-dimensional structures, the first physical property value, the second physical property value, the crystal structure, the primary, screening result and the secondary screening result. The client 100 displays the data d6 of the computation module 212.

Figure 8C:
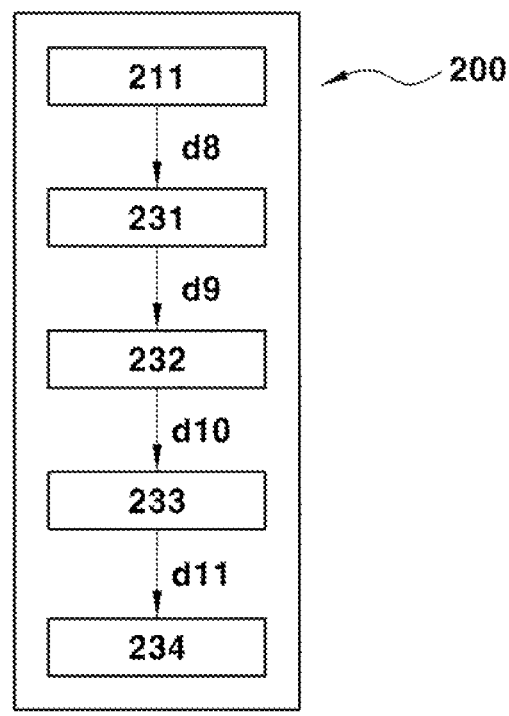
FIG. 8C is a schematic block diagram of a computation module, when the program for analyzing a sulfide-based solid electrolyte using computer simulation according to the embodiment simulates and analyzes a structure of a crystalline-structure sulfide-based solid electrolyte.

FIG. 8C is a schematic block diagram of the computation module 212, when the program 10 for analyzing a sulfide-based solid electrolyte using computer simulation according to the embodiment simulates and analyzes a structure of a crystalline-structure sulfide-based solid electrolyte.

Referring to FIGS. 7 and 8C, the program 10 for analyzing a sulfide-based solid electrolyte using computer simulation according to the embodiments ay analyze the crystalline-structure sulfide-based solid electrolyte.

FIG. 8C illustrates a program for simulating and analyzing a structure of a crystalline-structure sulfide-based solid electrolyte enabling a user to directly recognize how anion clusters and lithium ions are distributed in an area. The client directly receives a block value, so that direct recognition of the user can be improved. This will be described later in more detail.

Upon receiving information, the client 100 transmits input information D1 to the server 200. The client 100 receives a block value corresponding to a three-dimensional structure. The block value includes a network former, a network modifier, and a size of an area where the network former and the network modifier are disposed. The network former may be, for example, thiophosphate. The network modifier may be, for example, a lithium ion. The server 200 includes a simulation module 211, a first evaluation module 231, a first simulation module 232, a crystal structure definition module 233, and a physical property value calculation module 234. The simulation module 211 generates a three-dimensional structure corresponding to the block value. Upon receiving three-dimensional structure data d8 from the simulation module 211, the first evaluation module 231 evaluates a disposition type of an interior lattice of sulfur present in the sulfide-based solid electrolyte. Upon receiving first evaluation data d9 from the first evaluation module 231, the first simulation module 232 implements atom-based simulation. Upon receiving first simulation data d10 from the first simulation module 232, the crystal structure definition module 233 defines a crystal structure of the sulfide-based solid electrolyte. Upon receiving crystal structure data d11 from the crystal structure definition module 233, the physical property value calculation module 234 calculates a physical property value of the sulfide-based solid electrolyte by implementing electron-based simulation of the electrolyte, based on density functional theory.

The server 200 can feedback an implementation result to the client 100. The implementation result may include at least one of the three-dimensional structure, the internal lattice of sulfur, the first simulation, the crystal structure and the physical property value. The client 100 displays the implementation result.

Figure 8D:
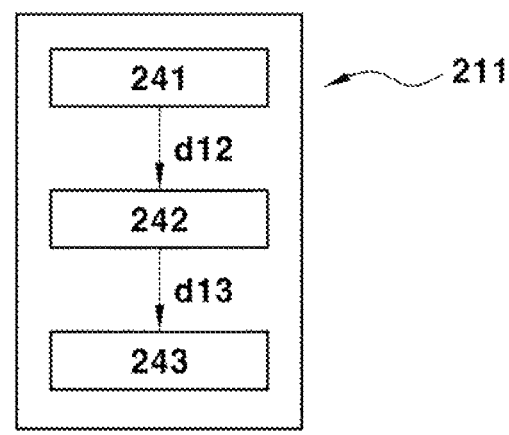
FIG. 8D is a schematic block diagram of a simulation module, when the program 10 for analyzing a sulfide-based solid electrolyte using computer simulation according to the embodiment analyzes generation of a glass-ceramic interface.

FIG. 8D is a schematic block diagram of the simulation module 211 when the program 10 for analyzing a sulfide-based bold electrolyte using computer simulation according to the embodiment analyzes generation of a glass-ceramic interface.

Referring to FIGS. 7 and 8D, the program 10 for analyzing a sulfide-based solid electrolyte us g computer simulation according to the embodiment may analyze generation of a glass-ceramic interface.

Upon receiving information, the client 100 transmits input information D1 to the server 200. At this time, the simulation module 211 includes a three-dimensional structure generation module 241, a structure generation module 242 and an image generation module 243. The three-dimensional structure generation module 241 generates a three-dimensional structure of a glassy-structure sulfide-based solid electrolyte and a three-dimensional structure of a crystalline-structure sulfide-based solid electrolyte. Upon receiving three-dimensional structure data d12 from the three-dimensional structure generation module 241, the structure generation module 242 generates a three-dimensional structure having an interface formed between the three-dimensional structure of the glassy-structure sulfide-based solid electrolyte and the three-dimensional structure of the crystalline-structure sulfide-based solid electrolyte bonded to each other certain direction. Upon receiving structure generation data d13 from the structure generation module 242, the image generation module 243 generates a cross-sectional image of the three-dimensional structure taken in a certain direction. Upon receiving data of the image from the image generation module 243, the client 100 displays the image.

Conventional programs for generating structures are auxiliary programs generally used for electron- and atom-based computer simulation. Most programs include only a structure for analyzing a certain property regarding calculation of material properties supporting internally. When the generation and analysis of the three-dimensional structure of sulfide-based solid electrolytes are carried out by electron or atom-based computer simulation, great amounts of calculation results are generated. In addition, arrangement of the enumerated results also requires great time and effort. Accordingly, there is a limitation of not supporting structural properties of sulfide-based solid electrolytes based on anion clusters.

With the program for analyzing a sulfide-based solid electrolyte using computer simulation according to the embodiment of the present invention, experimental phenomena can be easily and rapidly analyzed by electron- or atom-based computer simulation and thus new solid electrolyte materials can be designed. In addition, based on lithium ion conductivity, properties of sulfide-based solid electrolytes, which cannot be observed by experimentation, can be analyzed. Furthermore, properties of sulfide-based solid electrolytes can be analyzed without generating real prototypes.

Hereinafter the present invention will be described in more detail with reference to specific examples. The following examples are provided only for illustration and should not be construed s limiting the scope of the present invention.

Example 1

Method for Analyzing Glassy-Structure Sulfide-Based Solid Electrolyte

1. Setting Compositional Ratio

Parameter input includes three steps. Setting an initial parameter is a step of selecting a composition of a raw material powder. The compositional ratio of the raw material powder is represented by the following equation:

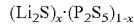

$(Li_2S)_x \cdot (P_2S_5)_{1-x}$ wherein x is a composition modifier. The composition modifier x that experimentally generates a lithium ion high-conduction phase is 0.6 to 0.9. The glassy generation algorithm limited the range of the composition modifier x from 0.4 to 1.0. When the composition modifier was determined, a type of molecular anion clusters derived from the network former, i.e., $P_xS_y$, was selected based on the determined composition. Anion clusters experimentally identified as network formers from glassy materials were $(PS_4)^{3-}$, $(P_2S_6)^{4-}$, and $(P_2S_7)^{4-}$. The network formers $(PS_4)^{3-}$, $(P_2S_6)$ and $(P_2S_7)^{4-}$ are represented by (1), (2) and (3) later, respectively. An additional vacant area to consider intermolecular gaps or voids that may be formed in the structure is designated by reference numeral 4. After selecting the network former to be included in the glassy structure, a ratio therebetween was selected. The ratio may be represented below:

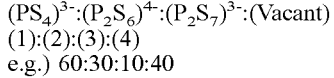

$(PS_4)^{3-}:(P_2S_6)^{4-}:(P_2S_7)^{3-}:(Vacant)$
(1):(2):(3):(4)
e.g.) 60:30:10:40

A total ratio of (1), (2) and (3) is 100. When a vacant area is present, the total ratio may be higher than 100. When the total ratio of (1), (2) and (3) is higher than 100, conversion is based on the total ratio of 100.

2. Generation and Division of Lattice Structure

Generation and division of lattice structure are shown in FIG. 2B. After determining the ratio, the size and shape of lattice were selected. The size of lattice could be determined by length i.e., a, b and c, and the type of figure could be determined by angles, i.e., α, β and γ (a, b and c are each positive rational numbers, and α, β and γ are each rational numbers indicating an angle of 0 to 180°). The size and shape of lattice could be freely selected. An internal spacing determining areas where the network formers are disposed in the set lattice was set. Regarding the settable spacing, a minimal spacing was determined by molecular size and a user can freely select from the minimal spacing to the maximum spacing.

3. Distribution of Thiophosphate Molecules and Lithium Ions

Network formers were randomly distributed along the set spacing. The positions of distributed network formers could be designated. Then, lithium ions were also randomly distributed in the lattice and the distributed lithium ions were subjected to a re-distribution process such that the distributed lithium ions were spaced from sulfur atoms by an appropriate distance. The positions of distributed lithium ions could be designated as well. In this case, lithium ions were randomly distributed at node points spaced by a predetermined distance in the interface created by the lattice, wherein the number of distributed lithium ions was determined in consideration of charge equilibrium.

4. Generation of Three-Dimensional Structure, Measurement of Physical Property Values, Screening and Result Values A three-dimensional structure was formed based on the distributed network formers and lithium ions. Physical property values were measured based on the three-dimensional structure, and screening with predetermined physical property values was carried out, based on the physical property values. After analysis was implemented by the server, a result value displayed by the client was shown in FIG. 6.

As apparent from the foregoing, with the method for analyzing a sulfide-based solid electrolyte using computer simulation and the program for analyzing a sulfide based solid electrolyte using computer simulation according to an embodiment of the present invention, properties of sulfide-based solid electrolytes, which cannot be observed by experimentation, can be analyzed, based on lithium ion conductivity.

With the method for analyzing a sulfide-based solid electrolyte using computer simulation and the program for analyzing a sulfide-based solid electrolyte using computer simulation according to an embodiment of the present invention, properties of sulfide-based solid electrolytes can be analyzed without generating real prototypes.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents. Hence, it should be construed that the aforementioned embodiments are exemplary and not limitative.

What is claimed is:

1. A method for analyzing a sulfide-based solid electrolyte using computer simulation comprising:
   connecting, by a user, to a client accessible server;
   inputting information of a sulfide-based solid electrolyte to be analyzed to the client;
   transmitting, by the client, the information to the server;
   implementing, by the server, generation of a three-dimensional structure in which anion clusters and lithium ions are disposed, based on the transmitted information;
   feeding back, by the server, an implementation result to the client; and
   displaying, by the client, the feedback result,
   wherein the method for analyzing a sulfide-based solid electrolyte using computer simulation is the method for simulating and analyzing a structure of a glassy-structure sulfide-based solid electrolyte,
   wherein the step of implementing comprises:
   generating, by a simulator of the server, the three-dimensional structure,
   calculating, by a computator of the server, a physical property value of the three-dimensional structure; and
   screening, by an inspector of the server, the sulfide-based solid electrolyte by comparing the physical property value with a predetermined reference physical property value in the server,
   wherein in the step of feeding back, the server feeds back a result of each of the three-dimensional structure, the physical property value and the screening to the client, and
   in the step of displaying the result, the client displays the result of each of the three-dimensional structure, the physical property value and the screening.

2. The method according to claim 1, wherein the method for analyzing a sulfide-based solid electrolyte using computer simulation comprises at least one of:
   a method for simulating and analyzing a structure of a glassy-structure sulfide-based solid electrolyte;
   a method for simulating and analyzing a structure of a crystalline-structure sulfide-based solid electrolyte; and
   a method for generating and analyzing a glass-ceramic interface.

3. The method according to claim 1, wherein, in the step of inputting, the information of the sulfide-based solid electrolyte comprises at least one of: a compositional ratio of $Li_2S$ and $P_2S_5$; a type of anion clusters, which are a network former; a compositional ratio of anion clusters; a size of an area where anion clusters and lithium ions, which are a network modifier, are distributed; a shape of the area where anion clusters and lithium ions are distributed; a size of a unit cell constituting the area where anion clusters and lithium ions are distributed; a distribution state of lithium ions; and a distribution state of anion clusters.

4. The method according to claim 1, wherein, in the step of calculating the physical property value, the computer calculates at least one of an energy of a three-dimensional structure, a mean squared displacement, a radial distribution function, a density and a type of an internal lattice of sulfur.

5. The method according to claim 1, wherein the method for analyzing a sulfide-based solid electrolyte using computer simulation is the method for simulating and analyzing a structure of a crystalline-structure sulfide-based solid electrolyte,
   wherein, in the step of inputting, a block value corresponding to a three-dimensional structure of the crystalline-structure sulfide-based solid electrolyte is input to the client,
   wherein the block value comprises a network former, a network modifier, and a size of an area where the network former and the network modifier are disposed,
   the step of implementing comprises:
   generating the three-dimensional structure corresponding to the block value;
   evaluating a disposition type of an interior lattice of sulfur;
   implementing atom-based simulation, based on an evaluation result of the interior lattice of sulfur;
   defining a crystal structure of the sulfide-based solid electrolyte, based on a result of the atom-based simulation; and
   calculating a physical property value of the sulfide-based solid electrolyte by implementing electron-based simulation of the sulfide-based solid electrolyte having the defined crystal structure, based on density functional theory.

6. The method according to claim 5, wherein, in the step of calculating the physical property value, the server calculates at least one of a total energy of the sulfide-based solid electrolyte, radial distribution function, mechanical property, electrical property, and the internal lattice of sulfur.

7. A method for analyzing a sulfide-based solid electrolyte using computer simulation comprising:
   connecting, by a user, to a client accessible to a server;
   inputting information of a sulfide-based solid electrolyte to be analyzed to the client;
   transmitting, by the client, the information to the server;
   implementing, by the server, generation of a three-dimensional structure in which anion clusters and lithium ions are disposed, based on the transmitted information;
   feeding back, by the server, an implementation result to the client; and
   displaying, by the client, the feedback result, wherein the method for analyzing a sulfide-based solid electrolyte using computer simulation is the method for simulating and analyzing a structure of a crystalline-structure sulfide-based solid electrolyte,
   wherein the step of implementing comprises:
   generating the three-dimensional structure;
   calculating, by a first computer of the server, a first physical property value of the three-dimensional structure of the sulfide-based solid electrolyte generated by the simulator, based on molecular dynamics;
   firstly screening, by a first inspector of the server, the sulfide-based solid electrolyte by comparing the first physical property value with a predetermined first reference physical property value in the server;
   defining, by a crystal structure definitor of the server, a crystal structure of the firstly screened sulfide-based solid electrolyte;
   calculating, by a second computer of the server, a second physical property value of the sulfide-based solid electrolyte having the defined crystal structure, based on density functional theory; and
   secondly screening, by a second inspector of the server, the sulfide-based solid electrolyte by comparing the second physical property value with a predetermined second reference physical property value in the server.

8. The method according to claim 7, wherein, in the step of calculating the first physical property value, the first computer calculates at least one of a total energy of the three-dimensional structure of the sulfide-based solid electrolyte, and a type of an internal lattice of sulfur.

9. The method according to claim 7, wherein, in the step of calculating the second physical property value, the second computer calculates at least one of a total energy of the sulfide-based solid electrolyte, an energy of an internal lattice of sulfur, mean squared displacement, electron structure, and migration energy barrier of lithium ions.

10. A method for analyzing a sulfide-based solid electrolyte using computer simulation comprising:
   connecting, by a user, to a client accessible to a server;
   inputting information of a sulfide-based solid electrolyte to be analyzed to the client;
   transmitting, by the client, the information to the server;
   implementing, by the server, generation of a three-dimensional structure in which anion clusters and lithium ions are disposed, based on the transmitted information;
   feeding back, by the server, an implementation result to the client, and displaying, by the client, the feedback result, wherein the method for analyzing a sulfide-based solid electrolyte is the method for generating and analyzing a glass-ceramic interface,
   wherein the step of the implementing comprises:
   generating a three-dimensional structure of a glassy-structure sulfide-based solid electrolyte, and a three-dimensional structure of a crystalline-structure sulfide-based solid electrolyte;
   generating a three-dimensional structure having an interface formed between the three-dimensional structure of the glassy-structure sulfide-based solid electrolyte and the three-dimensional structure of the crystalline-structure sulfide-based solid electrolyte bonded to each other in a certain direction; and
   generating a cross-sectional image of the three-dimensional structure taken in a certain direction,
   in the step of feeding back, the server feeds back the image to the client, and
   in the step of displaying, the client displays the image.

11. A system for analyzing a sulfide-based solid electrolyte using computer simulation comprising:
   a client for receiving information of a sulfide-based solid electrolyte and displaying an implementation result of a server; and
   a server for receiving the information from the client and feeding back the implementation result to the client,
   wherein the server comprises a simulator for generating a three-dimensional structure of the sulfide-based solid electrolyte, and
   anion clusters and lithium ions are disposed in the three-dimensional structures,
   wherein the system for analyzing a sulfide-based solid electrolyte using computer simulation simulates and analyzes a structure of a glassy-structure sulfide-based solid electrolyte,
   wherein the server further comprises:
   a computer, and
   an inspector,
   wherein the computer receives data of the three-dimensional structure of the sulfide-based solid electrolyte from the simulator and calculates a physical property value of the three-dimensional structure of the sulfide-based solid electrolyte, based on at least one theory of density functional theory and molecular dynamics, and
   the inspector receives data of the physical property value from the computator and screens the sulfide-based solid electrolyte by comparing the physical property value with a redetermined reference physical property value.

12. The system according to claim 11, wherein the system for analyzing a sulfide-based solid electrolyte using a computer simulator for implementing at least one of:
   simulating and analyzing a structure of a glassy-structure sulfide-based solid electrolyte;
   simulating and analyzing a structure of a crystalline-structure sulfide-based solid electrolyte; and
   generating and analyzing a glass-ceramic interface.

13. A system for analyzing a sulfide-based solid electrolyte using computer simulator comprising:
   a client for receiving information of a sulfide-based solid electrolyte and displaying an implementation result of a server; and
   a server for receiving the information from the client and feeding back the implementation result to the client,
   wherein the server comprises a simulator for generating a three-dimensional structure of the sulfide-based solid electrolyte, and
   anion clusters and lithium ions are disposed in the three-dimensional structure, wherein the program for analyzing a sulfide-based solid electrolyte using computer simulation simulates and analyzes a structure of a crystalline-structure sulfide-based solid electrolyte,
   wherein the server further comprises:
   a crystal structure definitor for receiving firstly screened data and defining a crystal structure of the sulfide-based solid electrolyte;
   a computor; and
   an inspector,
   wherein the computor comprises:
   a first computor for receiving data of the three-dimensional structure of the sulfide-based solid electrolyte from the simulator and calculating a first physical property value of the three-dimensional structure of the sulfide-based solid electrolyte, based on molecular dynamics; and
   a second computor for receiving data of the crystal structure from the crystal structure definitor and calculating a second physical property value of the sulfide-based solid electrolyte having the defined crystal structure, based on density functional theory,
   the inspector comprises:
   a first inspector for receiving data of the first physical property value from the first computor and firstly screening the sulfide-based solid electrolyte by comparing the first physical property value with a predetermined first reference physical property value; and
   a second inspector for receiving data of the second physical property value from the second computer and secondly screening the sulfide-based solid electrolyte by comparing the second physical property value with a predetermined second reference physical property value.

14. The system according to claim 13, wherein the program for analyzing a sulfide-based solid electrolyte using the computer simulator simulates and analyzes a structure of a crystalline-structure sulfide-based solid electrolyte,
   wherein the client receives a block value corresponding to the three-dimensional structure,
   the block value includes a network former, a network modifier, and a size of an area where the network former and the network modifier are disposed,
   wherein the server comprises:
   the simulator for generating the three-dimensional structure corresponding to the block value;
   a first evaluator for evaluating a disposition type of an interior lattice of sulfur present in the sulfide-based solid electrolyte;

a first simulator for receiving first evaluation data from the first evaluator and implementing atom-based simulation;

a crystal structure definitor for receiving first simulation data from the first simulator and defining a crystal structure of the sulfide-based solid electrolyte; and a physical property value calculator for receiving data of the crystal structure from the crystal structure definitor and calculating a physical property value of the sulfide-based solid electrolyte by implementing electron-based simulation of the electrolyte, based on density functional theory.

15. A system for analyzing a sulfide-based solid electrolyte using computer simulation comprising:

a client for receiving information of a sulfide-based solid electrolyte and displaying an implementation result of a server, and a server for receiving the information from the client and feeding back the implementation result to the client, wherein the server comprises a simulator for generating a three-dimensional structure of the sulfide-based solid electrolyte, and anion clusters and lithium ions are disposed in the three-dimensional structure, wherein the system for analyzing a sulfide-based solid electrolyte using computer simulation analyzes generation of a glass-ceramic interface, wherein the simulator comprises:

a three-dimensional structure generator for generating a three-dimensional structure of a glassy-structure sulfide-based solid electrolyte, and a three-dimensional structure of a crystalline structure sulfide-based solid electrolyte;

a structure generator for receiving data of the three-dimensional structure from the three-dimensional structure generator and generating a three-dimensional structure having an interface formed between the three-dimensional structure of the glassy-structure sulfide-based solid electrolyte and the three-dimensional structure of the crystalline-structure sulfide-based solid electrolyte bonded to each other in a certain direction; and an image generator for receiving data of the structure generation from the structure generator and generating a cross-sectional image of the three-dimensional structure taken in a certain direction, and the client receives data of the image from the image generator and displays the image.

* * * * *